United States Patent

Ueno et al.

Patent Number: 5,432,174
Date of Patent: Jul. 11, 1995

[54] TREATMENT OF OCULAR HYPERTENSION

[75] Inventors: Ryuji Ueno, Nishinomiya; Sachiko Kuno, Tokyo, both of Japan

[73] Assignee: R-Tech Ueno, Ltd., Osaka, Japan

[21] Appl. No.: 162,386

[22] Filed: Dec. 7, 1993

Related U.S. Application Data

[63] Continuation of Ser. No. 933,789, Aug. 24, 1992, abandoned.

[30] Foreign Application Priority Data

Mar. 19, 1992 [JP] Japan ................... 4-063316

[51] Int. Cl.$^6$ .................. A61K 31/535; A61K 31/47; A61K 31/34; A61K 31/215
[52] U.S. Cl. .................. 514/236.2; 514/309; 514/469; 514/530; 514/573; 514/652; 514/913
[58] Field of Search ............. 514/530, 573, 652, 913, 514/236.2, 309, 469

[56] References Cited

U.S. PATENT DOCUMENTS 4,952,581 8/1990 Bito et al. .................... 514/236.2

FOREIGN PATENT DOCUMENTS 0286903 10/1988 European Pat. Off.
0458590 5/1991 European Pat. Off.

OTHER PUBLICATIONS

Arch. Ophthalmol., vol. 108, No. 8, 1990, pp. 1102–1105.
Ophthalmology, vol. 98, No. 7, 1991, pp. 1079–1082.

*Primary Examiner*—Zohreh Fay
*Attorney, Agent, or Firm*—Sughrue, Mion, Zinn, Macpeak & Seas

[57] ABSTRACT

A method for the treatment of ocular hypertension which comprises administering, to a subject in need of such treatment,
(a) a β-adrenergic blocker at the enhancement phase of aqueous humor production, and
(b) a prostanoic acid compound at the suppression phase of aqueous humor production, and
in an amount effective in treatment of ocular hypertension.

7 Claims, No Drawings

TREATMENT OF OCULAR HYPERTENSION

This is a Continuation of application Ser. No. 07/933,789, filed Aug. 24, 1992, now abandoned.

BACKGROUND OF THE INVENTION

1. Field of the Invention

The present invention relates to the treatment of ocular hypertension with alternate administration of (a) a β-adrenergic blocker and (b) a prostanoic acid compound with an improved efficiency.

The compounds used as the component (b) in the present invention are prostaglandin analogues.

2. Information of Prior Art

It is well known that the production and effluence of the aqueous humor, which are the important factors for the circulation of the aqueous humor, and hence the intraocular pressure as the results thereof, vary with the circadian rhythm. Generally, in humans, the phase in which the aqueous humor production enhances is the daytime, during which the production of the aqueous humor is facilitated and the intraocular pressure rises. On the other hand, the phase in which the aqueous humor production suppresses is the night, during which the production of the aqueous humor is inhibited and the intraocular pressure falls. In contrast, in rabbits, the phase in which the aqueous humor production enhances is the night and the phase in which the aqueous humor production supresses is the daytime.

This circadian rhythm of the intraocular pressure is observed not only in healthy humans but also in subjects of ocular hypertension such as with glaucoma and a possibility that a relatively big variation in the intraocular pressure of hypertensive subjects may be an aggravating factor to the condition of disease has been noted. Accordingly, there is a continuous need for the development of an improved method for treatment of ocular hypertension in which the intraocular pressure is effectively controlled taking the circadian rhythm of ocular tension in the hypertensive subjects into consideration.

The β-adrenergic blockers are the most widely used drugs for the treatment of glaucoma and ocular hypertension. In a report studying a relation between the circadian rhythm of intraocular pressure and the ocular hypotensive activity of Timolol, a β-adrenergic blocker, it was observed that the activity of Timolol was significant in the enhancement phase of aqueous humor production, i.e. daytime in humans and night in rabbits, but negligible in the suppression phase of aqueous humor production, i.e. night in humans and daytime in rabbits. This fact indicates that there may be a possibility in which apparent (or observable) effect of β-adrenergic blockers such as Timolol is high at the enhancement phase of aqueous humor production and low at the suppression phase of aqueous humor production. However, in view of the facts that most of cause for the ocular hypertension lies in the inhibition of effluence of the aqueous humor and that controlling of the ocular hension is important for the treatment of ocular hypertension also in the suppression phase of aqueous humor production, it is considered that treating the ocular hypertension with a β-adrenergic blocker only is insufficient.

Prostanoic acid refers to the basic skeleton, shown by the formula below, as the common structural feature of the naturally occurring prostaglandins (hereinafter, prostaglandins are referred to as PGs).

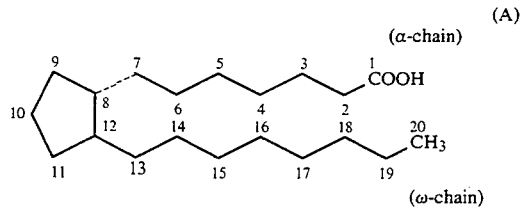

The primary PGs are classified based on the structural feature of the five-membered cycle moiety into PGAs, PGBs, PGCs, PGDs, PGEs, PGFs, PGGs, PGHs, PGIs and PGJs, and also on the presence or absence of unsaturation and oxidation in the chain moiety as:

Subscript 1—13,14-unsaturated-15-OH
Subscript 2—5,6- and 13,14-diunsaturated 15-OH
Subscript 3—5,6- 13,14- and 17,18-triunsaturated-15-OH Further, PGFs are sub-classified according to the configuration of hydroxy group at position 9 into α(hydroxy group being in the alpha configuration) and β(hydroxy group being in the beta configuration).

The fact that the above compounds under item (b) have ocular hypotensive activity has been known by Japanese Patent Publication No. A-108/1990. It has also been described in Japanese Patent Publication No. A-313728/1988, page 7, column 3, line 7 from bottom to page 8, column 4, line 4, that a combination of $PGF_2\alpha$ isopropyl ester and Timolol (an agent for treating glaucoma) may be advantageous because the ocular hypotensive activity of the former is not inhibited by a β-adrenergic blocker such as the latter. Furthermore, a synergistic combination of a β-adrenergic blocker and a 13,14-dihydro-15-keto-PG is described in EP-A-458590 (Nov. 27, 1991). Such description, however, does not suggest that an alternate use of the β-adrenergic blocker and the component (b) in the present invention gives an improved results.

After an extensive study the present inventor has surprisingly discovered that the prostanoic acid compounds exhibit a significant ocular hypotensive activity at the suppression phase of aqueous humor production in which the β-adrenergic blockers such as Timolol can hardly exhibit the ocular hypotensive activity.

SUMMARY OF THE INVENTION

In a first aspect, the present invention provides a method for the treatment of ocular hypertension which comprises ocularly administering, to a subject in need of such treatment, (a) a β-adrenergic blocker at the enhancement phase of aqueous humor production, and
(b) a prostanoic acid compound at the suppression phase of aqueous humor production, in an amount effective in treatment of ocular hypertension.

In a second aspect, the present invention provides an agent for the treatment of ocular hypertension, for alternate administration with a β-adrenergic blocker to be administered at the enhancement phase of aqueous humor production, comprising a prostanoic acid compound in an amount effective in treatment of ocular hypertension to be administered at the suppression phase of aqueous humor production.

In a third aspect, the present invention provides an agent for the treatment of ocular hypertension, for alternate administration with a prostanoic acid compound to be administered at the suppression phase of aqueous humor production, comprising a β-adrenergic blocker in an amount effective in treatment of ocular hypertension to be administered at the enhancement phase of aqueous humor production.

In a fourth aspect, the present invention provides an agent for the treatment of ocular hypertension, comprising (a) a β-adrenergic blocker to be administered at the enhancement phase of aqueous humor production and (b) a prostanoic acid compound to be administered at the suppression phase of aqueous humor production, the component (a) and (b) are contained in an amount effective in treatment of ocular hypertension in separate dosage forms.

In a fifth aspect, the present invention provides a package for the treatment of ocular hypertension, comprising a β-adrenergic blocker and a prostanoic acid compound in an amount effective in treatment of ocular hypertension with an indication for administering the β-adrenergic blocker at the enhancement phase of aqueous humor production and administering the prostanoic acid compound at the suppression phase of aqueous humor production.

DETAILED DESCRIPTION OF THE INVENTION

The β-adrenergic blockers used as the component (b) in the present invention refer to agents capable of blocking the β-adrenergic receptor. Typical examples of such agents are relatively less selective β-adrenergic receptor blocking agents which are represented by the following formula:

A-OCH$_2$CH(OH)CH$_2$NHC(CH$_3$)(R)

wherein A is an aromatic group and R is hydrogen atom or methyl.

The above group A includes 4-morpholino-1,2,5-thiadiazol-3-yl, 2-acetylbenzofuran-7-yl, 1,2,3,4-tetrahydro-2-oxo-quinoline-5-yl. Preferred compounds include Timolol, Befunolol, Betaxolol, Levabunolol, Carteolol and pharmaceutically acceptable salts thereof such as inorganic salts, e.g. hydrochloride or organic salts, e.g. maleate.

The term prostanoic acid compound refers to a compound (or derivative) in which one or more atom or group (or moiety) in the prostanoic acid shown by the formula (A) is replaced by other atom or group or eliminated. Such derivatization includes the modifications known in the synthetic PG analogues such as those shown below and other modifications. The preferred prostanoic acid compounds have the ocular hypotensive activity and particularly aqueous humor effluence enhancing activity.

Nomenclature

Nomenclature of the prostanoic acid compounds herein uses the numbering system of prostanoic acid represented in formula (A) shown above.

While formula (A) shows a basic skeleton having twenty carbon atoms, the compounds used in the present invention are not limited to those having the same number of carbon atoms. The carbon atoms in Formula (A) are numbered 2 to 7 on the α-chain starting from the α-carbon atom adjacent to the carboxylic carbon atom which is numbered 1 and towards the five-membered ring, 8 to 12 on the said ring starting from the carbon atom on which the α-chain is attached, and 13 to 20 on the ω-chain starting from the carbon atom adjacent to the ring. When the number of carbon atoms is decreased in the α-chain, the number is deleted in order starting from position 2 and when the number of carbon atoms is increased in the α-chain, compounds are named as substituted derivatives having respective substituents at position 1 in place of carboxy group (C-1). Similarly, when the number of carbon atoms is decreased in the ω-chain, the number is deleted in order starting from position 20 and when the number of carbon atoms is increased in the ω-chain, compounds are named as substituted derivatives having respective substituents at position 20. Stereochemistry of the compounds is the same as that of above formula (A) unless otherwise specified.

The above formula expresses a specific configuration which is the most typical one, and in this specification compounds having such a configuration are expressed without any specific reference to it.

In general, PGDs, PGEs and PGFs have a hydroxy group on the carbon atom at position 9 and/or 11 but the compounds used in the present invention includes PGs having a group other than a hydroxyl group at position 9 and/or 11. Such PGs are referred to as 9-dehydroxy-9-substituted-PG compounds or 11-dehydroxy-11-substituted-PG compounds.

As stated above, nomenclature of the prostanoic acid compounds is based upon the prostanoic acid. These compounds, however, can also be named according to the IUPAC naming system. For example, 13,14-dihydro-15-keto-16R,S-fluoro-PGE$_2$ is (Z)-7-{(1R,2R,3R)-3-hydroxy-2-[(4R,S)-fluoro-3-oxo-1-octyl]-5-oxocyclopentyl}-hept-5-enoic acid. 13,14-dihydro-15-keto-20-ethyl-11-dehydroxy-11R-methyl-PGE$_2$ methyl ester is methyl (Z)-7-{(1R,2R,3R)-3-methyl-2-[3-oxo-1-decyl]-5-oxocyclopentyl}-hept-5-enoate. 13,14-dihydro-6,15-diketo-19-methyl-PGE$_2$ ethyl ester is ethyl 7-{(1R,2S,3S)-3-hydroxy-2-(7-methyl-3-oxo-1-octyl)-5-oxocyclopentyl}-6-oxoheptanoate. 13,14-dihydro-15-keto-20-ethyl-PGF$_{2\alpha}$ isopropyl ester is isopropyl (Z)-7-[(1R,2R,3R,5S)-3,5-dihydroxy-2-{3-oxo-1-decyl)-cyclopentyl]-hept-5-enoate. 13,14-dihydro-15-keto-20-methyl-PGF$_{2\alpha}$ methyl ester is methyl (Z)-7-[(1R,2R,3R,5S)-3,5-dihydroxy-2-{3-oxo-1-nonyl}-cyclopentyl]-hept-5-enonate.

Preferred Compounds

Preferred prostanoic acid derivatives used in the present invention are those having an oxo group at position 15 of the prostanoic acid in place of the hydroxy group as a feature. These derivatives may have a single bond (15-keto-PG$_1$ compounds), a double bond (15-keto-PG$_2$ compounds) between positions 5 and 6, or two double bonds (15-keto-PG$_3$ compounds) between positions 5 and 6 as well as positions 17 and 18.

Examples of substitution products or derivatives include pharmaceutically or physiologically acceptable salts and esters at the carboxy group at the alpha chain, unsaturated derivatives having a double bond or a triple bond between positions 2 and 3 or positions 5 and 6, respectively, substituted derivatives having substituent(s) on carbon atom(s) at position 3, 6, 16, 17, 19 and/or 20 and compounds having lower alkyl or a hydroxy (lower) alkyl group at position 9 and/or 11 in place of the hydroxy group, of the above PGs.

Examples of substituents present in preferred compounds are as follows: Substituents on the carbon atom at position 3, 17 and/or 19 include lower alkyl, for example, C$_{1-4}$ alkyl, especially methyl and ethyl. Substituents on the carbon atom at position 16 include lower alkyl e.g. methyl, ethyl etc., hydroxy and halogen atom e.g. chlorine, fluorine, aryloxy e.g. trifluoromethylphenoxy, etc. Substituents on the carbon atom at position 20 include saturated and unsaturated lower alkyl e.g. $C_{1-4}$ alkyl, lower alkoxy e.g. $C_{1-4}$ alkoxy and lower alkoxy (lower) alkyl e.g. $C_{1-4}$ alkoxy-$C_{1-4}$ alkyl. Substituents on the carbon atom at position 6 include oxo group forming carbonyl. Stereochemistry of PGs having hydroxy, lower alkyl or lower (hydroxy) alkyl substituent on the carbon atom at position 9 and/or 11 may be alpha, beta or mixtures thereof.

Said derivatives may have an alkoxy, phenoxy or phenyl group at the end of the omega chain where the chain is shorter than the primary PGs.

Especially preferred compounds are those having a lower alkyl such as methyl, ethyl, etc. at position 20.

A group of preferred compounds used in the present invention has the formula

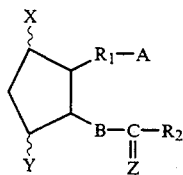 (I)

wherein X and Y are hydrogen, hydroxy, halo, lower alkyl, hydroxy(lower)alkyl, or oxo, with the proviso that at least one of X and Y is a group other than hydrogen, and 5-membered ring may have at least one double bond, A is —COOH or its pharmaceutically acceptable salt or ester, B is —CH$_2$—CH$_2$—, —CH=CH— or —C≡C—,

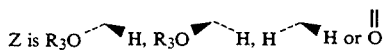

wherein R$_3$ is lower alkyl or acyl, R$_1$ is bivalent saturated or unsaturated, lower or medium aliphatic hydrocarbon residue which is unsubstituted or substituted with halo, oxo or aryl, R$_2$ is saturated or unsaturated, medium aliphatic hydrocarbon residue which is unsubstituted or substituted with halo, hydroxy, oxo, lower alkoxy, lower alkanoyloxy, cyclo(lower)alkyl, aryl or aryloxy.

In the above formula, the term "unsaturated" in the definitions for R$_1$ and R$_2$ is intended to include at least one and optionally more than one double bond and/or triple bond isolatedly, separately or serially present between carbon atoms of the main and/or side chains. According to usual nomenclature, an unsaturation between two serial positions is represented by denoting the lower number of said two positions, and an unsaturation between two distal positions is represented by denoting both of the positions. Preferred unsaturation is a double bond at position 2 and a double or triple bond at position 5.

The term "lower or medium aliphatic hydrocarbon residue" or "medium aliphatic hydrocarbon residue" refers to a straight or branched chain hydrocarbyl group having 1 to 14 carbon atoms or 5 to 14 carbon atoms, respectively, (for a side chain, 1 to 3 carbon atoms being preferred) and preferably 2 to 8 carbon atoms for R$_1$ and 6 to 9 carbon atoms for R$_2$.

The term "halo" denotes fluoro, chloro, bromo and iodo.

The term "lower" throughout the specification is intended to include a group having 1 to 6 carbon atoms unless otherwise specified.

The term "lower alkyl" as a group or a moiety in hydroxy(lower)alkyl, monocyclic aryl(lower) alkyl, monocyclic aroyl(lower)alkyl or halo(lower)alkyl includes saturated and straight or branched chain hydrocarbon radicals containing 1 to 6, carbon atoms, e.g. methyl, ethyl, propyl, isopropyl, butyl, isobutyl, t-butyl, pentyl and hexyl.

The term "lower alkoxy" refers to the group lower-alkyl-O— wherein lower alkyl is as defined above.

The term "hydroxy(lower)alkyl" refers to lower alkyl as defined above which is substituted with at least one hydroxy group, e.g. hydroxymethyl, 1-hydroxyethyl, 2-hydroxyethyl and 1-methyl-1-hydroxyethyl.

The term "lower alkanoyloxy" refers to a group of the formula: RCO—O— wherein RCO— is an acyl group formed by oxidation of a lower alkyl group as defined above, e.g. acetyl.

The term "cyclo(lower)alkyl" refers to a cyclic group formed by cyclization of a lower alkyl group as defined above.

The term "aryl" includes unsubstituted or substituted aromatic carbocyclic or heterocyclic (preferably monocyclic) groups, e.g. phenyl, tolyl, xylyl and thienyl. Examples of substituents are halo and halo(lower)alkyl wherein halo and lower alkyl being as defined above.

The term "aryloxy" refers to a group of the formula: ArO—wherein Ar is aryl as defined above.

Suitable "pharmaceutically acceptable salts" includes conventional non-toxic salts, and may be a salt with an inorganic base, for example an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt, caffeine salt, etc.), a basic amino acid salt (e.g. arginine salt, lysine salt, etc.), tetraalkyl ammonium salt and the like. These salts can be prepared by the conventional process, for example from the corresponding acid and base or by salt interchange.

Examples of the "pharmaceutically acceptable esters" are aliphatic esters, for example, lower alkyl ester e.g. methyl ester, ethyl ester, propyl ester, isopropyl ester, butyl ester, isobutyl ester, t-butyl ester, pentyl ester, 1-cyclopropylethyl ester, etc., lower alkenyl ester e.g. vinyl ester, allyl ester, etc., lower alkynyl ester e.g. ethynyl ester, propynyl ester, etc., hydroxy(lower) alkyl ester e.g. hydroxyethyl ester, lower alkoxy(lower)-alkyl ester e.g. methoxymethyl ester, 1-methoxyethyl ester, etc., and aromatic esters, for example, optionally substituted aryl ester e.g. phenyl ester, tosyl ester, t-butylphenyl ester, salicyl ester, 3,4-di-methoxyphenyl ester, benzamidophenyl ester etc., aryl(lower)alkyl ester e.g. benzyl ester, trityl ester, benzhydryl ester, etc. These esters may be prepared by convenitonal esterification starting from the corresponding acid and alcohol or ester exchange.

Preferred examples of A include —COOH, —COOCH$_3$, —COOCH$_2$CH$_3$ and —COOCH(CH$_3$)$_2$.

The configuration of the ring and the α- and/or omega chain in the above formula (I) may be the same as or different from that in the primary PGs. However, the present invention also includes a mixture of a compound having a primary configuration and that of an unprimary configuration.

A group of more preferred compounds used in the present invention has the formula

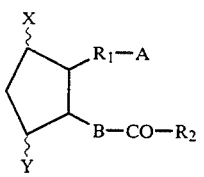

wherein X and Y are hydrogen, hydroxy, halo, lower alkyl, hydroxy(lower)alkyl, or oxo, with the proviso that at least one of X and Y is a group other than hydrogen, and 5-membered ring may have at least one double bond, A is —COOH or its pharmaceutically acceptable salt or ester, B is —CH$_2$—CH$_2$—, —CH=CH— or —C≡C—, R$_1$ is bivalent saturated or unsaturated, lower or medium aliphatic hydrocarbon residue which is unsubstituted or substituted with halo, oxo or aryl, R$_2$ is saturated or unsaturated, medium aliphatic hydrocarbon residue having 5 or more carbon atoms in the main or straight chain moiety which is unsubstituted or substituted with halo, hydroxy, oxo, lower alkoxy, lower alkanoyloxy, cyclo(lower)alkyl, aryl or aryloxy.

Examples of the typical compounds of the present invention are 15-keto-20-loweralkyl-PGA-Fs and their Δ$^2$-derivatives, 3R,S-methyl-derivatives, 6-oxo-derivatives, 5R,S-fluoro-derivatives, 5,5-difluoro-derivatives, 16R,S-methyl-derivatives, 16,16-dimethyl-derivatives, 16R,S-fluoro-derivatives, 16,16-difluoro-derivatives, 17S-methyl-derivatives, 17R,S-fluoro-derivatives, 17,17-difluoro-derivatives and 19-methyl-derivatives.

The compounds having 15-keto group may be in the keto-hemiacetal equilibrium by forming a hemiacetal between hydroxy group at position 11 and ketone at position 15.

The proportion of both tautomeric isomers, when present, varies depending on the structure of the rest of the molecule or kind of any substituent present and, sometimes, one isomer may predominantly be present in comparison with the other. However, in this invention, it is to be appreciated that the compounds used in the invention include both isomers. Further, while the compounds used in the invention may be represented by a structure or name based on keto-form regardless of the presence or absence of the isomers, it is to be noted that such structure or name does not intend elimination of the hemiacetal type of compounds.

In the present invention, any of the individual tautomeric isomers, a mixture thereof, or optical isomers, a mixture thereof, a racemic mixture, and other isomers such as steric isomers can be used in the same purpose.

Some of the compounds used in the present invention may be prepared by the method disclosed in Japanese Patent Publications (unexamined) No. A-108/1990 and A-96528/1990.

Alternatively, these compounds may be prepared by a process analogous to that described in the above publications in combination with the known synthetic method for the five-membered ring moiety.

In the process for preparing 13,14-dihydro-15-keto-compound:

A commercially available (—)-Corey lactone, which is used as a starting material, is subjected to Collins oxidation to give an aldehyde. The aldehyde is allowed to react with dimethyl(2-oxoalkyl)phosphonate anion to give an α,β-unsaturated ketone, and the resultant is reduced to ketone. The carbonyl group of the ketone is allowed to react with a diol to give a ketal, thereby protected, then a corresponding alcohol is obtained by elimination of the phenylbenzoyl group, and the resulting hydroxy group is protected with dihydropyran to give a tetrapyranyl ether. Thus, precursors of PGs wherein the ω-chain is 13,14-dihydro-15-keto-alkyl can be obtained.

Using the above tetrapyranyl ether as a starting material, 6-keto-PG$_1$s of the formula:

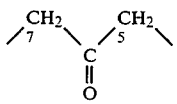

may be obtained as follows: The tetrapyranyl ether is reduced using diisobutyl aluminium hydride and the like to give a lactol, which is allowed to react with a ylide obtained from (4-carboxybutyl)triphenylphosphonium bromide, and the resultant is subjected to esterification followed by cyclization, combining the 5,6-double bond and the C-9 hydroxyl group with NBS or iodine, providing a halide. The resultant is subjected to dehydrohalogenation with DBU and the like to give a 6-keto compound, which is subjected to Jones oxidation followed by deprotection to give the objective compound.

Further, PG$_2$s of the formula:

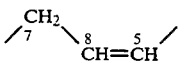

may be obtained as follows: The above tetrapyranyl ether is reduced to the lactol, which is allowed to react with a ylide obtained from (4-carboxybutyl)triphenylphosphonium bromide to give a carboxylic acid. The resultant is subjected to esterification followed by Jones oxidation and deprotection to give the objective compound.

In order to obtain PG$_1$s of the formula:

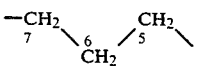

using the above tetrapyranyl ether as a starting material, in the same manner as PG$_2$ of the formula:

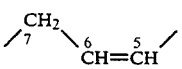

the 5,6-double bond of the resulting compound is subjected to catalytic reduction followed by deprotection. To prepare 5,6-dehydro-PG$_2$s containing a hydrocarbon chain of the formula:

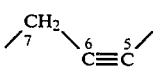

a monoalkyl copper complex or a dialkyl copper complex of the formula:

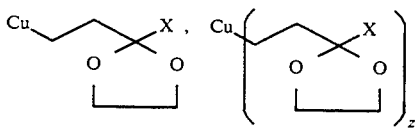

is subjected to 1,4-addition with 4R-t-butyldimethyl-silyloxy-2-cyclopenten-1-one, and the resulting copper enolate is seized with 6-carboalkoxy-1-iodo-2-hexyne or a derivative thereof.

PGs containing a methyl group instead of a hydroxy group at the C-11 position may be obtained as follows: PGA obtained by Jones oxidation of the hydroxy group at the C-9 position of the 11-tosylate is allowed to react with a dimethyl copper complex to give 11-dehydroxy-11-methyl-PGE. Alternatively, an alcohol obtained after elimination of p-phenylbenzoyl group is converted to a rosylate. An unsaturated lactone obtained by DBU treatment of the tosylate is converted to a lactol. After introduction of an α-chain using Wittig reaction, the resulting alcohol (C-9 position) is oxidized to give PGA. PGA is allowed to react with dimethyl copper complex to give 11-dehydroxy-11-methyl-PGE. The resultant is reduced using sodium borohydride and the like to give 11-dehydroxy-11-methyl-PGF.

PGs containing a hydroxymethyl group instead of a hydroxyl group at the C-11 position is obtained as follow: 11-dehydroxy-11-hydroxymethyl-PGE is obtained by a benzophenone-sensitized photoaddition of methanol to PGA. The resultant is, for example, reduced using sodium borohydride to give 11-dehydroxy-11-hydroxymethyl-PGF.

16-Fluoro-PGs may be obtained using dimethyl (3-fluoro-2-oxoalkyl)phosphonate anion in the preparation of an α,β-unsaturated ketone. Similarly, 19-methyl-PGs may be obtained using a dimethyl (6-methyl-2-oxoalkyl)phosphonate anion.

The preparations in the present invention are not construed to be limited to them, and suitable means for protection, oxidation, reduction and the like may be employed.

Examples of the preparation of the prostanoic acid compounds are described in the Japanese Patent Publications (unexamined) No. A-151552/1989, A-108/1990, A-96528/1990 and A-96529/1990.

The β-adrenergic blockers and the prostanoic acid compounds used in the present invention can be used for the treatment of various disease and conditions of humans and animals in which lowering of ocular pressure is desirous and are usually administered systemically or topically by, for example, ophthalmic, oral, intravenous, subcutaneous, rectal administration etc.

As used herein, the term "treatment" or "treating" refers to any means of control of a disease in a mammal, including preventing the disease, curing the disease, relieving the disease and arresting or relieving the development of the disease.

While the dosage varies depending on the kind, age, weight, condition of the patient, such as humans or animals, severity of the disease, purpose of the treatment, judgement of the physician and route or period of administration, usually a satisfactory effect is obtained within the range of 0.01–500 μg/eye of the β-adrenergic blocker and 0.001–500 mg/kg of the prostanoic acid compound.

The agents used in the present invention can be administered in the form of a pharmaceutical composition containing the active components and optionally other ingredients, such as carrier, diluent or excipient.

Such composition includes liquids such as ophthalmic solution, emulsion, dispersion etc. and semisolids such as gel, ointment etc.

Diluents for the aqueous solution or suspension include, for example, distilled water and physiological saline. Diluents for the nonaqueous solution and suspension include, for example, vegetable oils e.g. olive oil, liquid paraggine, mineral oil, and propylene glycol and p-octyldodecanol. The composition may also contain isotonization agents such as sodium chloride, boric acid, sodium citrate, etc. to make isotonic with the lacrimal fluid and buffering agents such as borate buffer, phosphate buffer, etc. to maintain pH about 5.0 to 8.0. Further, stabilizers such as sodium sulfite, propylene glycol, etc., chelating agents such as sodium edetate, etc., thickeners such as glycerol, carboxymethylcellulose, carboxyvinyl polymer, etc. and preservatives such as methyl paraben, propyl paraben, etc. may also be added these can be sterilized e.g. by passing through a bacterial filter or by heating.

The ophthalmic ointment may contain vaseline, Plastibase, Macrogol, etc. as a base and surfactant for increasing hydrophilicity. It may also contain gelling agents such as carboxymethylcellulose, methylcellulose, carboxyvinyl polymer, etc.

In addition, the composition may contain antibiotics such as chloramphenicol, penicillin, etc. in order to prevent or treat bacterial infection.

These composition may be packaged with an indication for administration. Such indication may be printing on package box, a bottle, a label, a separate paper sheet etc.

A more complete understanding of the present invention can be obtained by reference to the following Preparation Examples, Formulation Examples and Test Examples which are provided herein for purpose of illustration only and are not intended to limit the scope of the invention.

Preparations

Preparations of 13,14-dihydro-15-keto-20-ethyl-PGA$_2$ isopropyl ester, 13,14-dihydro-15-keto-20-ethyl-PGE$_2$ isopropyl ester and 13,14-dihydro-15-keto-20-ethyl-PGF$_2\alpha$ isopropyl ester (cf. Preparation chart I):

1) Preparation of 1S-2-oxa-3-oxo-6R-(3-oxo-1-trans-decenyl)-7R-(4-phenylbenzoyloxy)-cis-bicyclo[3.3.0]-octane (3):

Commercially available (−)-Corey lactone (1) (7 g) was subjected to Collins oxidation in dichloromethane to give aldehyde (2). The resultant was allowed to react with dimethyl(2-oxononyl)phosphonate (4.97 g) anion to give 1S-2-oxa-3-oxo-6R-(3,3-ethylendioxy-1-trans-decenyl)-7R-(4-phenylbenzoyloxy)-cis-bicyclo[3.3.0]-octane (3).

2) Preparation of 1S-2-oxa-3-oxo-6R-(3-oxodecyl)-7R-(4-phenylbenzoyloxy)-cis-bicyclo[3.3.0]-octane (4):

Unsaturated ketone (3) (7.80 g) was reduced in ethyl acetate (170 ml) using 5% Pd/C under hydrogen atmosphere. The product obtained after the usual work-up (4) was used in the following reaction.

3) Preparation of 1S-2-oxa-3-oxo-6R-(3,3-ethylene-dioxy-decyl)-7R-(4-phenylbenzoyloxy)-cis-bicyclo[3.3.0]-octane (5):

Saturated ketone (4) was converted to ketal (5) in dry benzene (150 ml) using ethylene glycol and p-toluenesulfonic acid (catalytic amount).

4) Preparation of 1S-2-oxa-3-oxo-6R-(3,3-ethylenedioxy-decyl)-7R-hydroxy-cis-bicyclo[3.3.0]-octane (6):

To a solution of ketal (5) in absolute methanol (150 ml) was added potassium carbonate (2.73 g). The mixture was stirred overnight at room temperature. After neutralization with acetic acid, the resultant was concentrated under reduced pressure. The resulting crude product was extracted with ethyl acetate. The organic layer was washed with a dilute aqueous solution of sodium bicarbonate and a saline, and dried. The crude product obtained after evaporation was chromatographed to give alcohol (6). Yield; 3.31 g 5) Preparation of lactol (7):

Alcohol (6) (0.80 g) was reduced in dry toluene (8 ml) using DIBAL-H at −78° C. to give lactol (7).

6) Preparation of 13,14-dihydro-15,15-ethylenedioxy-20-ethyl-PGF$_2\alpha$ (8):

A DMSO solution of lactol (7) was added to ylide prepared from (4-carboxybutyl)triphenylphosphonium bromide (3.65 g). The reaction mixture was stirred overnight to give carboxylic acid (8).

7) Preparation of 13,14-dihydro-15,15-ethylenedioxy-20-ethyl-PGF$_2\alpha$ isopropyl ester (9):

Carboxylic acid (8) was converted to 13,14-dihydro-15,15-ethylenedioxy-20-ethyl-PGF$_2\alpha$ isopropyl ester (9) using DBU and isopropyl iodide in acetonitrile.

Yield; 0.71 g

8) Preparation of 13,14-dihydro-15-keto-20-ethyl-PGF$_2\alpha$ isopropyl ester (10):

13,14-dihydro-15,15-ethylenedioxy-20-ethyl-PGF$_2\alpha$ isopropyl ester (9) (0.71 g) was kept in acetic acid/THF/water (3/1/1) at 40° C. for 3 hours. The crude product obtained after concentration under reducted pressure was chromatographed to give 13,14-dihydro-15-keto-20-ethyl-PGF$_2\alpha$ isopropyl ester (10).

Yield; 0.554 g

9) Preparation of 13,14-dihydro-15-keto-20-ethyl-PGA$_2\alpha$ isopropyl ester (12):

A solution of 13,14-dihydro-15-keto-20-ethyl-PGF$_2\alpha$ isopropyl ester (10) (0.125 g) and p-toluenesulfonyl chloride (0.112 g) in pyridine (5 ml) was maintained at 0° C. for 2 days. According to the usual work-up, tosylate (11) was obtained.

Tosylate (11) was subjected to Jones oxidation in acetone (8 ml) at −25° C. The crude product obtained after the usual work-up was chromatographed to give 13,14-dihydro-15-keto-20-ethyl-PGA$_2\alpha$ isopropyl ester (2).

Yield; 0.060 g

10) Preparation of 13,14-dihydro-15,15-ethylenedioxy-20-ethyl-11-t-butyldimethylsiloxy-PGF$_2\alpha$ isopropyl ester (13):

13,14-dihydro-15,15-ethylenedioxy-20-ethyl-PGF$_2\alpha$ isopropyl ester (9) (3.051 g) was dissolved in dry N,N-dimethylformamide (25 ml), t-butyldimethylsilyl chloride (1.088 g) and imidazole (0.49 g) was added thereto. The resultant was stirred at room temperature overnight. The reaction mixture was concentrated under reduced pressure, and the resulting crude product was chromatographed to give 13,14-dihydro-15,15-ethylenedioxy-20-ethyl-11-t-butyldimethylsiloxy-PGF$_2\alpha$ isopropyl ester (13).

Yield; 2.641 g

11) Preparation of 13,14-dihydro-15,15-ethylenedioxy-20-ethyl-11-t-butyldimethylsiloxy-PGE$_2$ isopropyl ester (14):

13,14-dihydro-15,15-ethylenedioxy-20-ethyl-11-t-butyldimethylsiloxy-PGF$_2\alpha$ isopropyl ester (13) (1.257 g) was subjected to Jones oxidation at −40° C. After the usual work-up, the resulting crude product was chromatographed to give 13,14-dihydro-15,15-ethylenedioxy-20-ethyl-11-t-butyldimethylsiloxy-PGE$_2$ isopropyl ester (14).

Yield; 1.082 g

12) Preparation of 13,14-dihydro-15-keto-20-ethyl-PGE$_2$ isopropyl ester (15):

To a solution of 13,14-dihydro-15,15-ethylene-dioxy-20-ethyl-11-t-butyldimethylsiloxy-PGE2$\alpha$ isopropyl ester (14) in acetonitrile was added hydrofluoric acid (46% aqueous solution). The mixture was stirred at room temperature for 40 minutes. The crude products obtained after usual work-up was chromatographed to give 13,14-dihydro-15-keto-20-ethyl-PGE$_2$ isopropyl ester (15).

Yield; 0.063 g (97%)

Preparation Chart

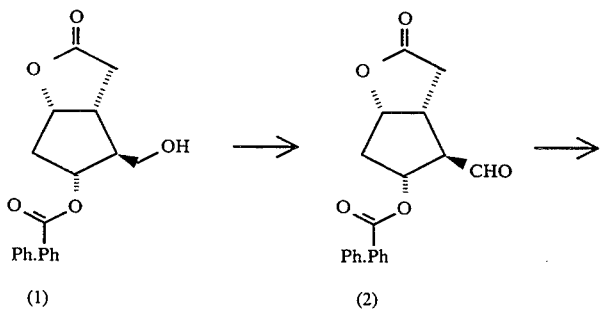

-continued
Preparation Chart
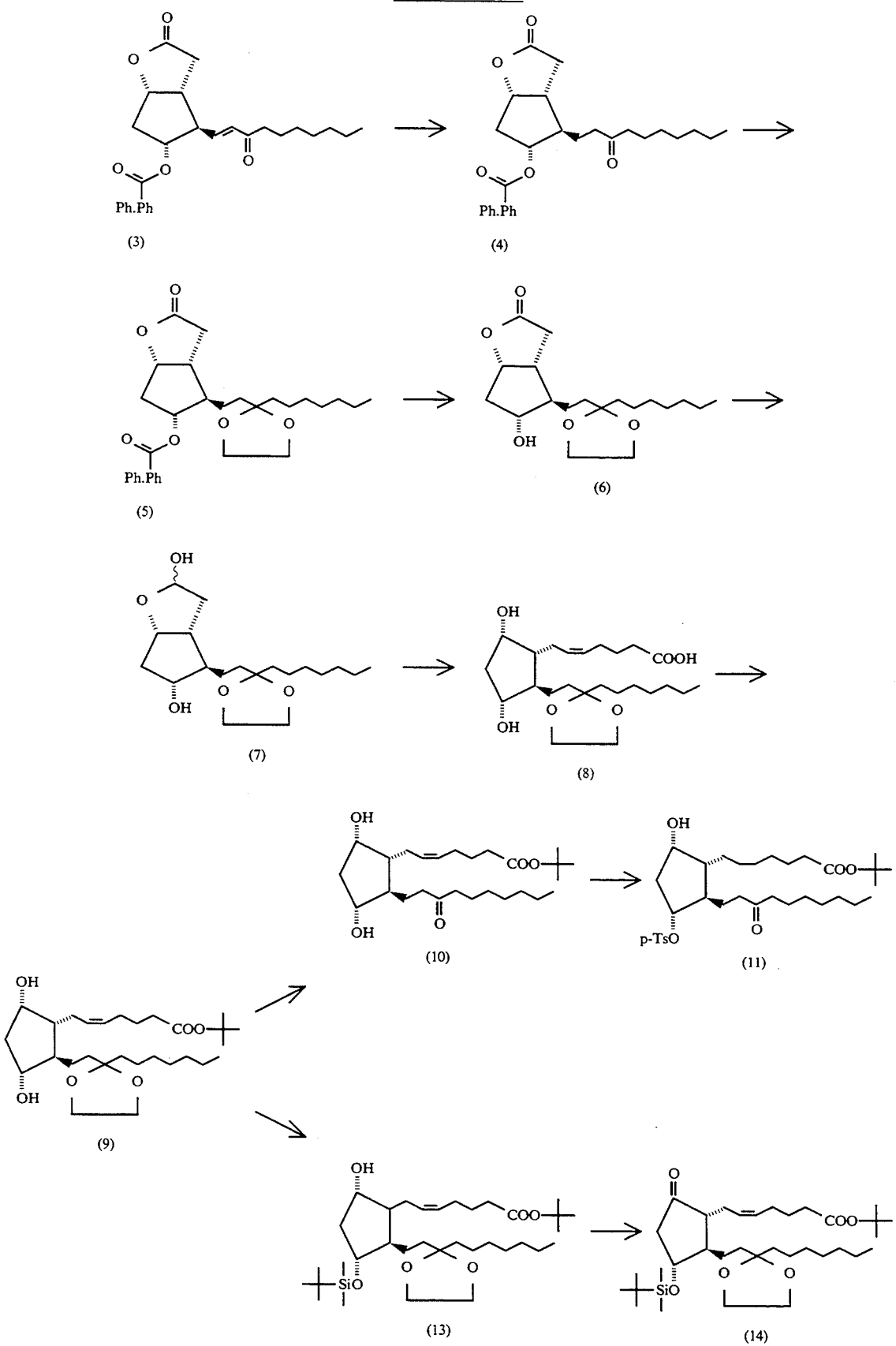

-continued
Preparation Chart

(11) → 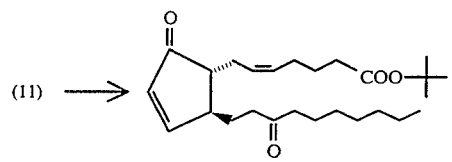

(12)

(14) → 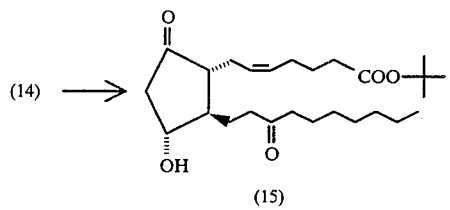

(15)

 : Iso-propyl

Formulation Example 1

| Timolol maleate | 0.1 g |
|---|---|
| Physiological saline | q.s. to 100 ml |

Formulation Example 2

| 13,14-dihydro-15-keto-20-ethyl-PGF$_2\alpha$ isopropyl ester | 0.01 g |
|---|---|
| Nonion Surfactant | 1.0 g |
| Physiological saline | q.s. to 100 ml |

Test Example 1

Hypotensive effect of Timolol was evaluated in the enhancement phase of aqueous humor production and the suppression phase of aqueous humor production of rabbits. Since the circadian rhythm of rabbits, different from that of humans, has the enhancement phase of aqueous humor production at night and the suppression phase of aqueous humor production at daytime, the following two experiments were performed.

(1) Enhancement phase of aqueous humor production:

White rabbits (n=8) were used in the experiment of intraocular pressure measurement after keeping under the environmental conditions including a light and darkness cycle consisting of a light period from 21:00 to 9:00 and a dark period from 9:00 to 21:00 for more than one week. In the experiment, 35 μl of a 0.5% Timolol eyedrop (Trademark: Timoptol) was administered to one eye at 11:00 (dark time). The ocular tension was measured immediately before and 1 hour after the administration and the difference between the obtained two values was expressed as decrease in intraocular pressure (ΔIOP).

(2) Suppression phase of aqueous humor production:

White rabbits (n=12) were used in the experiment of intraocular pressure measurement after keeping under the environmental conditions including a light and darkness cycle consisting of a light period from 8:00 to 20:00 and a dark period from 20:00 to 8:00 for more than one week. In the experiment, 35 μl of a 0.5% Timolol eyedrop (Trademark: Timoptol) was administered to one eye at 10:00 (light time). The ocular tension was measured immediately before and 3 hours after the administration and the difference between the obtained two values was expressed as decrease in intraocular pressure (ΔIOP). The results are shown in Table 1.

TABLE 1

| | Enhancement Phase* | Suppression Phase* |
|---|---|---|
| ΔIOP (mmHg) | 6.4 ± 1.0 | 2.5 ± 0.8 |

*Production of aqueous humor

Then, the procedure of the experiment (2) was repeated except that a 0.12% eye drop of 13,14-dihydro-15-keto-20-ethyl-PGF$_2\alpha$ isopropyl ester was used in place of the 0.5% Timolol eye drop. The results are shown in Table 2.

TABLE 2

| | Suppression Phase* |
|---|---|
| ΔIOP (mmHg) | 7.1 ± 0.7 |

*See footnote of Table 1.

Test Example 2

A 0.5% Timolol eye drop was intraocularly administered to subjects of glaucoma (n=8) twice (morning and evening) a day for 4 weeks. Differences in intraocular pressure were measured as in Test Example 1 and expressed as decrease in intraocular pressure (ΔIOP). The results are shown in Table 3.

TABLE 3

| | Enhancement Phase* (11:00) | Suppression Phase* (19:00) |
|---|---|---|
| ΔIOP (mmHg) | 2.9 ± 0.8 | 0.4 ± 0.7 |

*See footnote of Table 1.

Separately, the above experiment was repeated using subjects of glaucoma (n=10) and administering a 0.12% eye drop of 13,14-dihydro-15-keto-20-ethyl-PGF$_2\alpha$ isopropyl ester in place of the 0.5% Timolol eye drop and decrease in intraocular pressure (ΔIOP) was determined at the suppression phase of aqueous humor production (19:00). The results are shown in Table 4.

TABLE 4

| | Suppression Phase* |
|---|---|
| ΔIOP (mmHg) | 2.1 ± 0.3 |

*See footnote of Table 1.

What we claim is:

1. A method for the treatment of ocular hypertension which comprises administering, to a subject in need of such treatment,
   (a) a β-adrenergic blocker during the enhancement phase of aqueous-humor production and not during the suppression phase of aqueous humor production, and
   (b) a 15-keto prostaglandin compound during the suppression phase of aqueous-humor production, and in an amount effective in treatment of ocular hypertension.

2. The method according to claim 1, wherein the 15-keto-prostaglandin compound is a prostaglandin F compound.

3. The method according to claim 1, wherein the β-adrenergic blocker is selected from the group consisting of Timolol, Befunolol, Betaxolol, Levobunolol, Carteolol and pharmaceutically acceptable salt thereof.

4. The method according to claim 1 for the treatment of glaucoma.

5. A method for the treatment of ocular hypertension which comprises administering, to a human in need of such treatment,
   (a) a β-adrenergic blocker at daytime when the phase of aqueous-humor production is enhancing, and
   (b) a 15-keto-prostaglandin compound at night when the phase of aqueous-humor production is suppressing, and in an amount effective in treatment of ocular hypertension.

6. The method according to claim 1, wherein the β-adrenergic agent is administered to the subject only during the enhancement phase of aqueous-humor production and the 15-keto-prostaglandin compound is administered to the subject only during the suppression phase of aqueous-humor production.

7. The method according to claim 1, wherein the 15-keto-prostaglandin compound has the following formula:

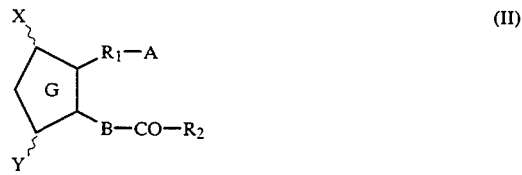

wherein X and Y are hydrogen, hydroxy, halo, lower alkyl, hydroxy(lower)alkyl, or oxo, with the proviso that at least one of X and Y is a group other than hydrogen, and the 5-membered ring G may have at least one double bond, A is —COOH or its pharmaceutically acceptable salt or ester, B is —CH$_2$CH$_2$—, —CH═CH— or —C≡C—, R$_1$ is bivalent saturated or unsaturated, lower or medium aliphatic hydrocarbon residue which is unsubstituted or substituted with halo, oxo or aryl, R$_2$ is saturated or unsaturated, medium aliphatic hydrocarbon residue having 5 or more carbon atoms in its main or straight chain moiety which is unsubstituted or substituted with halo, hydroxy, oxo, lower alkoxy, lower alkanoyloxy, cyclo(lower)alkyl, aryl or aryloxy.

* * * * *